United States Patent [19]

Decker et al.

[11] 4,196,147
[45] Apr. 1, 1980

[54] MANUFACTURE OF N-ALKYLANILINES

[75] Inventors: Martin Decker, Ludwigshafen;
Herwig Hoffmann, Frankenthal;
Leopold Hupfer, Friedelsheim;
Herbert Toussaint, Frankenthal, all of Fed. Rep. of Germany

[73] Assignee: BASF Aktiengesellschaft, Fed. Rep. of Germany

[21] Appl. No.: 837,938

[22] Filed: Sep. 29, 1977

[30] Foreign Application Priority Data

Oct. 14, 1976 [DE] Fed. Rep. of Germany ....... 2646379

[51] Int. Cl.² ............................................. C07C 85/06
[52] U.S. Cl. ................................................. 260/577
[58] Field of Search ........................................ 260/577

[56] References Cited

U.S. PATENT DOCUMENTS

| | | | |
|---|---|---|---|
| 2,813,124 | 11/1957 | Rice et al. | 260/577 |
| 3,316,261 | 4/1967 | Speranza et al. | 260/577 X |
| 4,082,802 | 4/1978 | Nakagawa et al. | 260/577 X |

FOREIGN PATENT DOCUMENTS

| | | | |
|---|---|---|---|
| 1155136 | 10/1963 | Fed. Rep. of Germany | 260/577 |
| 2061709 | 6/1971 | Fed. Rep. of Germany | 260/577 |

*Primary Examiner*—John Doll
*Attorney, Agent, or Firm*—Keil & Witherspoon

[57] ABSTRACT

N-Alkylanilines are obtained by alkylating anilines with alcohols in the absence of hydrogen under a pressure substantially higher than the autogenous pressure of the reaction mixture, at from 50° to 250° C., preferably in the presence of a fixed catalyst containing cobalt, nickel and copper.

7 Claims, No Drawings

MANUFACTURE OF N-ALKYLANILINES

The present invention relates to a process for the manufacture of N-alkylanilines by reacting a primary or secondary alcohol with aniline or its nuclear-substituted homologs in the presence of a hydrogenating catalyst.

The reaction on which the process is based, and which falls into the category of aminating and alkylating reactions (replacement of hydroxyl by amino; cf. Houben-Weyl, 4th edition, volume 11/1, pages 126 et seq.) has been disclosed.

The specific object of alkylating aromatic amines of the aniline type presents the special problem that the aromatic amines are relatively easily hydrogenated in the nucleus; the conventional auxiliary measure for controlling the N-alkylation reactions, namely the use of hydrogen in the presence of hydrogenating catalysts, therefore as a rule gives nuclear-hydrogenated products or, at the very least, by-products.

Experience has shown that only Raney nickel is suitable, and sufficiently active at low temperatures, to allow the use of hydrogen to be dispensed with (cf. British Pat. No. 314,872). However, Raney nickel cannot be used as a fixed bed catalyst, so that certain methods of carrying out the process continuously cannot be used with Raney nickel.

We have found that the process referred to at the outset can be very successfully carried out continuously (continuous operation being made possible, inter alia, by the use of a fixed bed catalyst), if the reaction is carried out substantially in the absence of hydrogen, at a pressure of not less than 100 bars and at from 150° to 250° C. The use of a catalyst which contains, for example, cobalt, nickel and copper on a carrier, and which may or may not be a fixed catalyst, is preferred. Other suitable catalysts are, for example, those containing cobalt, manganese and phosphoric acid on a carrier, with or without an alkali metal oxide or an alkaline earth metal oxide, and catalysts based on mixtures of nickel, copper and chromium.

Of course, the fact that the process is carried out continuously is not an essential feature of the invention; rather, the process can, where required, also be carried out batchwise.

Advantageously, the process is carried out under a pressure of from 100 to 300 bars, preferably from 150 to 250 bars, which can be maintained in a technologically advantageous manner by means of a buffer of adequately compressed inert gas (nitrogen or argon). Operation under purely hydraulic pressure, i.e. in the absence of a gas phase, is also possible provided the available equipment permits this.

As is shown by the investigation below, there is no sharp limit at which the use of higher pressure becomes effective; rather, the yield of the desired products gradually decreases when the pressure is lowered, for example from 200 bars through 100 bars and finally to, for example, 25 bars. No explanation of this observation has hitherto been provided; rather, it is surprising that such an effect should exist since even a pressure of 50 bars sufficed in every case to keep the reaction mixture in the liquid phase at the stated reaction temperature.

A possible post-facto explanation may be provided on the basis of the conventional concept that the N-alkylation by means of alcohols takes place with intermediate formation of an aldehyde and hydrogen, the aldehyde undergoing adduct formation with the amine to give a Schiff base, which is immediately hydrogenated to the secondary amine, in accordance with equations (1) to (3):

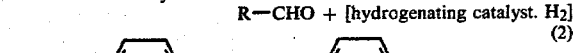
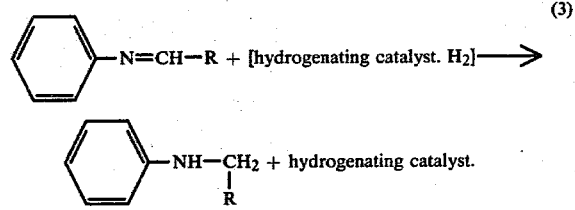

It may be assumed that instead of the desired hydrogenation of the Schiff base, gaseous hydrogen is liberated (and then serves to hydrogenate the nucleus) if the prevailing pressure is too low.

However, this concept is in no way intended to limit the invention.

For the purposes of the invention, anilines means aniline and its nuclear-alkylated substitution products (toluidines and xylidines). Primary and secondary alcohols means aliphatic, cycloaliphatic or araliphatic alcohols of, in general, from 1 to 15, preferably from 1 to 10, carbon atoms, the aniline derivatives of which alcohols are of industrial significance. N-alkylated aromatic amines are above all required as intermediates for the manufacture of dyes.

The term "substantially in the absence of hydrogen" means, for the purposes of the invention, that hydrogen in the conventional amounts (e.g. corresponding to partial pressures of from 1 to 300 bars) is not added. The presence of small amounts of hydrogen, for example in accordance with the above theoretical concept, may be disregarded.

The reactants are in general consumed in the stoichiometric ratio and are employed in proportions corresponding thereto. An excess of the amine or alcohol, for example an up to 2-fold excess of either, in general has no effect on the result and is only important with regard to economy of operation (recovery and recycling of excess material), the presence of some excess amine resulting in almost complete conversion of the alcohol with the formation of only small amounts of the N,N-dialkylamino compound.

In the Examples which follow, the amounts and ratios are by weight, unless stated otherwise.

EXAMPLE 1

0.5 part by volume of a catalyst containing 10% of cobalt, 10% of nickel and 4% of copper on alumina (all amounts being calculated as oxides) is located in a pressure-resistant tubular reactor. The catalyst is first reduced at 240° C. by means of hydrogen under atmospheric pressure. A nitrogen pressure of 200 bars is then set up and per hour 0.1 part by weight of a mixture of aniline and n-butanol in the molar ratio of 1.25:1 is fed to the reactor at 200° C., whilst 200 parts by volume of off-gas are released. In each case the pressure is maintained by a supply of nitrogen. The reaction mixture obtained has the following composition: 68.6% of N- butylaniline, 24.2% of aniline and 2.3% of butanol. The yield is 97.5 mole%, based on aniline converted.

EXAMPLE 2

A mixture of aniline and isobutanol in the molar ratio of 1.25:1 is reacted under the conditions of Example 1, but at 190° C. At a throughput of 0.1 part by weight of the mixture per hour a yield of 95.7 mole% of N-isobutylaniline, again based on aniline converted, is found.

If the throughput is increased to 0.2 part by weight per hour, the yield is 95.3 mole%; if the reaction temperature is raised to 210°–220° C., the yield is from 92 to 93 mole%. Each of the figures is calculated as above.

EXAMPLE 3

340 parts by volume of the catalyst described in Example 1 are located in a high pressure reactor suitable for industrial reactions and, per hour, a mixture of 64.6 parts by weight of o-toluidine and 21.9 parts by weight of ethanol is reacted at 190° C. under a nitrogen pressure of 200 bars. The ratio of the reactants corresponds to a 27 mole% excess of o-toluidine. To control the heat balance, 200,000 parts by volume of the gas which serves to maintain the pressure are circulated per hour through the reactor by means of a pump.

After removing the water formed in the reaction, 77.2 parts by weight per hour of a reaction mixture containing 51.4% of N-ethyl-toluidine, 39.3% of o-toluidine and 4.3% of N,N-diethyl-o-toluidine are obtained. The yield of the desired N-ethyl-o-toluidine is 91.9 mole%; diethyl-o-toluidine is formed in an amount of 6.3 mole%.

In sustained operation, the diethyltoluidine formed as a by-product can be recovered and admixed to the starting materials, in which case it reacts with o-toluidine to give N-monoethyl-o-toluidine.

EXAMPLE 4

A catalyst containing 12% of cobalt, 0.77% of manganese and 0.6% of phosphoric acid on pumice as a carrier is employed in the apparatus described in Example 1, in the corresponding amount. On carrying out the reaction described in detail in Example 1, the present catalyst gives a mixture of from 42 to 45% by weight of N-ethyl-o-toluidine, from 44 to 50% of unconverted toluidine, 5% of N,N-diethyl-o-toluidine and from 4 to 5% of ethyl alcohol. The yield of N-ethyl-o-toluidine, based on o-toluidine converted, is from 87 to 89 mole%.

EXAMPLE 5

The following experiment was carried out to illustrate the effect of the operating pressure on the outcome of the reaction.

0.5 part by volume of the catalyst described in Example 1 are introduced into the experimental equipment described in Example 1 and a mixture of o-toluidine and ethyl alcohol in the molar ratio of 1.25:1 is reacted at a certain rate per hour. The reaction temperature is in every case 220° C., but the pressure is varied from 25 to 250 bars by forcing in the corresponding amounts of nitrogen. The amount of off-gas is in each case set to 50 liters (S.T.P.) per hour. The outcome of the reaction is recorded in the Table which follows.

| Experiment | Reaction pressure (bar) | Reaction mixture, parts/h | Water removed, parts/h | $H_2O$ in the organic phase (Fischer method) % | Residue % | Analysis by gas chromatography (% of area) | | | | | Yield in mole % based on o-toluidine converted |
|---|---|---|---|---|---|---|---|---|---|---|---|---|
| | | | | | | Ethanol | MCHA* | o-toluidine | DET* | ET* | Unknown | |
| 1 | 25 | 2.24 | 0.179 | 1.03 | 13.0 | 0.64 | 1.21 | 41.30 | 2.92 | 38.45 | 2.48 | 64.6 |
| 2 | 50 | 2.11 | 0.176 | 1.13 | 9.7 | 0.40 | 1.84 | 39.34 | 2.14 | 42.82 | 2.76 | 70.6 |
| 3 | 100 | 2.43 | 0.205 | 0.88 | 9.2 | 0.66 | 2.29 | 29.58 | 3.62 | 52.50 | 2.74 | 70.6 |
| 4 | 200 | 2.32 | 0.181 | 0.78 | 2.0 | 0.92 | 1.98 | 33.35 | 5.88 | 55.90 | — | 84.6 |

*MCHA = 2-Methyl-1-cyclohexylamine
DET = Diethyltoluidine
ET = Ethyltoluidine

We claim:

1. A process for the manufacture of an N-alkylaniline by reacting a primary or secondary alcohol with aniline or a nuclear-substituted homolog thereof, in the presence of a catalyst which consists essentially of cobalt, manganese and phosphoric acid, with or without small amounts of an alkali metal oxide or an alkaline earth metal oxide, comprising:
   carrying out the reaction with said catalyst supported on a carrier, at a temperature of from 50° to 250° C., and substantially in the absence of hydrogen, and at a pressure of not less than 100 bars, said pressure being maintained by means of an inert gas compressed to the reaction pressure.

2. A process as claimed in claim 1, in which the reaction is carried out continuously in the presence of a fixed carrier supported catalyst.

3. A process as claimed in claim 1, in which the inert gas used to maintain the reaction pressure is selected from the group consisting of nitrogen and argon.

4. A process as claimed in claim 1, in which the reaction pressure is about 150 to 250 bars.

5. A process as claimed in claim 4, in which the inert gas used to maintain the reaction pressure is selected from the group consisting of nitrogen and argon.

6. A process as claimed in claim 1, in which the reaction temperature is from about 150° to 250° C.

7. A process as claimed in claim 6, in which the reaction pressure is about 100 to 300 bars.

* * * * *